US008735702B1

(12) United States Patent
Miles

(10) Patent No.: US 8,735,702 B1
(45) Date of Patent: May 27, 2014

(54) PORTABLE DISSIPATING MEDIUM USED FOR REMOVAL OF VIBRATIONAL INTERFERENCE IN A BOWED STRING OF A VIOLIN FAMILY INSTRUMENT

(76) Inventor: Deborah R. Miles, Boulder, CO (US)

( * ) Notice: Subject to any disclaimer, the term of this patent is extended or adjusted under 35 U.S.C. 154(b) by 0 days.

(21) Appl. No.: 13/561,307

(22) Filed: Jul. 30, 2012

Related U.S. Application Data

(60) Provisional application No. 61/613,896, filed on Mar. 21, 2012.

(51) Int. Cl.
*G10G 5/00* (2006.01)
(52) U.S. Cl.
USPC .................................................. 84/327
(58) Field of Classification Search
USPC .................................................. 84/327
See application file for complete search history.

(56) References Cited

U.S. PATENT DOCUMENTS

| | | | | | |
|---|---|---|---|---|---|
| 915,345 | A | * | 3/1909 | Gould | 84/280 |
| 1,288,179 | A | * | 12/1918 | Poehland | 84/280 |
| 2,444,280 | A | * | 6/1948 | Burhans | 84/294 |
| 2,498,459 | A | * | 2/1950 | Schroetter | 84/280 |
| 2,974,556 | A | * | 3/1961 | Fawick | 84/280 |
| 3,160,050 | A | * | 12/1964 | Klein | 84/327 |
| 3,598,011 | A | * | 8/1971 | Henkle | 84/280 |
| 3,769,871 | A | * | 11/1973 | Cawthorn | 84/291 |
| D230,425 | S | * | 2/1974 | Rosen | D17/20 |
| 4,018,129 | A | * | 4/1977 | Hollander | 84/294 |
| 4,037,505 | A | * | 7/1977 | Maples | 84/280 |
| 4,316,402 | A | * | 2/1982 | Goldner | 84/280 |
| 4,334,455 | A | * | 6/1982 | Beecher | 84/302 |
| 5,003,858 | A | * | 4/1991 | Rowell | 84/280 |
| 5,069,102 | A | * | 12/1991 | Wolf | 84/280 |
| 5,817,959 | A | * | 10/1998 | Kagan | 84/280 |
| 5,889,222 | A | * | 3/1999 | Burgess | 84/453 |
| 6,127,611 | A | * | 10/2000 | VansEvers | 84/294 |
| 6,696,626 | B1 | * | 2/2004 | Pagenkopf | 84/280 |
| 7,304,225 | B2 | * | 12/2007 | Ricci | 84/302 |
| 7,449,625 | B2 | * | 11/2008 | Johnson et al. | 84/302 |
| 7,482,518 | B1 | * | 1/2009 | DiSanto | 84/291 |
| 7,687,695 | B2 | * | 3/2010 | DeJule | 84/270 |

(Continued)

OTHER PUBLICATIONS

Lost wolf, James Lawson, Internet Cello Society Fourms>Instruments and Equipment> Lost wolf, posted Jun. 3, 2012, viewed on Oct. 30, 2013 at http://cellofun.yuku.com/reply/73593.*
Firth, I. M., The wolf tone in the cello: Acoustic and holographic studies, KTH Computer Science and Communications.*
Freiberg, Sarah, How to Tame Annoying Howling Wolf Tones, Strings, Instruments, Care and Maintenance May 2005, viewed Nov. 1, 2013 at http://www.allthingsstrings.com/Instruments/CARE-MAINTENANCE/How-to-Tame-Annoying-Howling-Wolf-Tones.*
Castagna, et al., Relationships between compressional-wave and shear-wave velocities, Geophysics, vol. 50 No. 4 (Apr. 1985, p. 571-581.*

*Primary Examiner* — Robert W Horn
(74) *Attorney, Agent, or Firm* — Edwin H. Crabtree; Ramon L. Pizarro

(57) ABSTRACT

A dissipating medium made of a stone-like tile. The tile used for removing a wolf note and its related energy, when played on a string musical instrument. The tile is made of a natural mineral, such as travertine. Also, the tile has a shear wave velocity between 300 to 440 m/sec. The tile can have an angular or annular shape. The angular shape is in a range of 10 to 12 inches square and a thickness in a range of ½ to ¾ inch. A top surface of the tile includes an annular depression for receiving an end pin of a cello's tail piece. The medium can be constructed of two tiles with an upper tile 10 inches square and a lower tile 12 inches square. Also, the medium has a weight in a range of 6 to 12 pounds for ease in transporting.

15 Claims, 2 Drawing Sheets

(56) References Cited

U.S. PATENT DOCUMENTS

| | | | |
|---|---|---|---|
| 7,915,505 B2 * | 3/2011 | Miniaev | 84/291 |
| 7,982,111 B2 * | 7/2011 | Fuller et al. | 84/173 |
| 2005/0235806 A1 * | 10/2005 | Alberti | 84/327 |
| 2009/0188370 A1 * | 7/2009 | DeJule | 84/294 |
| 2010/0050850 A1 * | 3/2010 | Rahe | 84/174 |

* cited by examiner

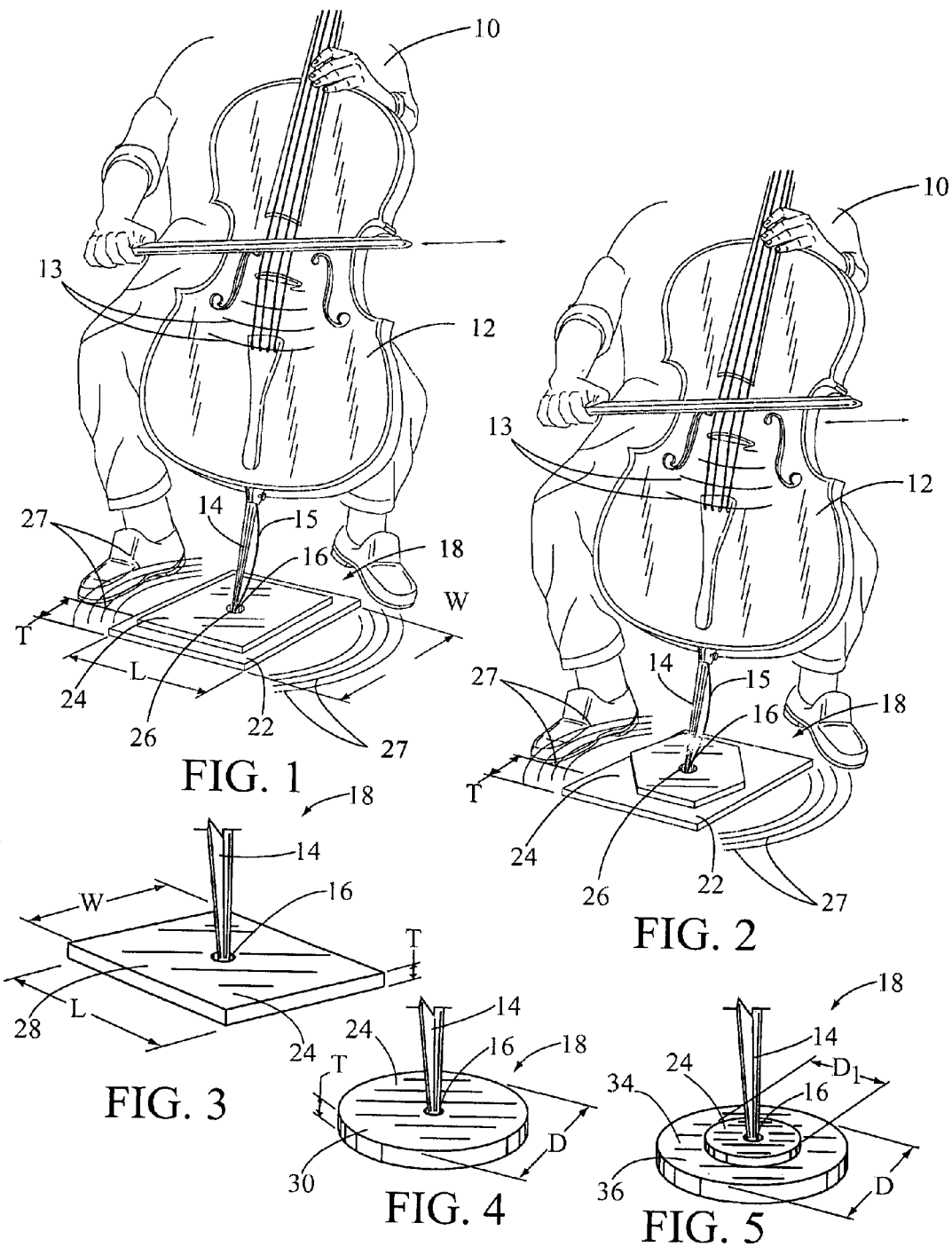

PORTABLE DISSIPATING MEDIUM USED FOR REMOVAL OF VIBRATIONAL INTERFERENCE IN A BOWED STRING OF A VIOLIN FAMILY INSTRUMENT

This non-provisional utility patent application claims the benefit of a provisional patent application Ser. No. 61/613,896, filed on Aug. 1, 2012, by the subject inventor, and having a title of "Removal of Vibrational Interference in the Bowed String of a Violin Family Instrument Using a Dissipating Medium".

REFERENCES CITED

1. Aitchison, Robin, 2010, Wolf Notes, http://www.aitchison-cellos.com/articlewolf.htm
2. Benade, Arthur H. 1976, Fundamentals of Musical Acoustics, Oxford University Press, London
3. Clayton, Chris, 1998, "Who's Afraid of the Big bad Wolf?", Internet Cello Society, www.cello.org, tips
4. Cremer, Lothar, 1983, Translation by John S. Allen, The Physics of the Violin, MIT Press Cambridge, Mass.
5. Cremer, L., and M. Heckl, 1988, Translation by E. E. Ungar, Structure-Borne Sound, Springer-Verlag, Berlin Heidelberg, New York, London, Paris, Tokyo
6. Davis, Evan, 2010, An Overview "fly by" of the Structural Acoustics of the Violin, presented at Oberlin Acoustic Workshop, June, 2010.
7. Davis, Evan, 2010, SEA Studies, presented to Oberlin Acoustics Workshop, June, 2010.
8. Fletcher, Neville H., Rossing, Thomas, D., 1991, The Physics of Musical Instruments, Springer-Verlag; Berlin Heidelberg, New York, London, Paris, Tokyo
9. Gough, Collin, 1980, The Resonant Response of a Violin G String and the Excitation of the Wolf-note; Acoustica, vol 44, p 113.
10. Gough, Collin, 1988, The Acoustics of Stringed Instruments Studied by String Resonances, CAS, no 35, pp 22-28.
11. Gough, Collin, 2010, Rocking Bridge and Island Area, presented to Oberlin Acoustics Workshop, June, 2010
12. Lehmann, Gottfried, and Lehmann, Matthias, 2000, Experiences and Observances on the Effectiveness of a Procedure for Vibration Treatment of String Instrument. Translated by Henry Strobel and Lothar Tews, 2001, Henry Strobel, Violin Maker & Publisher, Oregon.
13. McIntyre, M. E. & Woodhouse, J, 1978, The Acoustics of Stringed Musical Instruments, Interdisciplinary Science Reviews, Vol. 3, No. 2, 1978, pp 157-173.
14. Pickering, Norman, Sep. 7, 2005, "The Wolf Note", a paper distributed at the Oberlin Acoustics Workshop, June 2010.
15. Pickering, Norman, 1991, The Bowed String, Amereon, LTD, Mattituk, New York.
16. Ramaseshan, S, 1988, "Scientific Papers of C V Raman", Indian Academy of Sciences, Bangalore, India—Papers used:
    I. Raman, C V, 1909, The Small Motion At Nodes Of A Vibrating String, Nature (London) vol 82, p. 9 (collection p. 1)
    II. Raman, C V, 1911, Photographs Of Vibration Curves, Philos. Mag. Vol 21 pp 615-18 (collection p. 5-8)
    III. Raman, C V, 1914, The Dynamic Theory Of The Motion Of Bowed Strings, Bull. Indian Assoc. Cultiv. Sci. vol 11, pp 43-52. (collection pp. 220-9)
    IV. Raman, C V, 1916, On The "Wolf-Note" Of The Violin And 'Cello, Nature(London) vol 97, pp 362-3. (collection p. 230-1)
    V. Raman, C V, 1918, On the mechanical theory of the vibrations of bowed strings and of musical instruments of the violin family, with experimental verification of results—Part 1, Bull. Indian AssocCultiv. Sci vol 15, pp1-158. (collection p. 243-389)
    VI. Raman, C V, 1918, The Wolf-note in pizzicato playing, Nature (London) vol 101, p 264. (collection p. 242)
    VII. Raman, C V, 1910, The Maintenance of Forced Oscillations, Nature (London) vol 82, pp 428-9. (collection p. 4)
17. Reumont, Geehard, 1996, How To Improve The Resonance Conditions Of Musical Instruments By Vibration De-damping. Translated by Lothar Tews, Henry Strobel, Violin maker and Publisher, Oregon.
18. Schleske, Martin, 2003, Violin Acoustics Handbook—"Fingerboard Acoustics in Tonal Adjustment of a violin"; www.schleske.com
19. White, G. W. 1915, The Origin Of The Wolf-Note In Bowed String Instruments, Proc. Phil Soc 18, p 85.
20. Woodhouse, J. and P. M. Galluzzo, 2004, The Bowed String As We know It Today, ACTA Acustica united with Acustica, Vol 90, pp 597-589.

BACKGROUND OF THE INVENTION (a) Field of the Invention

This invention relates to broadly to a dissipating medium used with a bowed string musical instrument, and more particularly, but not by way of limitation, to a portable dissipating medium made of a material with a shear wave velocity between 300 to 400 m/sec, one such material being a stone-like natural mineral tile. The tile received on a floor surface with the top of the tile used to engage an end pin of a tail piece on a musical instrument, such as a cello. The dissipating medium removes an interfering vibration or energy of a "wolf note", which manifest as an unevenness or a beating sound at a certain frequency of the instrument.

(b) Discussion of Prior Art

Heretofore, members of an acoustical violin family of bowed instruments, the most popular being a violin, a viola, a violoncello or cello, and a double bass, all have a note or frequency which either beats or is suddenly louder, called a "wolf note", by musicians and luthiers. Experts in the field of bowed instrument construction believe the wolf note is caused by coupled oscillations within the body and strings of the instrument.

In the research of the cause and effect of the wolf note, there has been found no prior references or prior art patents that suggest or teach the removal of interfering energy of the wolf note using a portable dissipating medium for engaging the end pin of the cello's tail piece. Further, there are no prior art references that suggest or teach that the wolf note energy is a different type of wave motion, such as shear and compressive wave motion, and therefore can be dissipated through the end pin, while allowing certain wave motions, shear waves or compression waves, to return back into the body of the cello, which correspond to the length of the string. The current thinking is that the musical strings are excited by the bow in a form of Helmholtz motion. The strings then mechanically excite the bridge which excites the body of the instrument. All motions of the bridge and the body of the instrument are believed to be either compressional, also called acoustic or longitudinal waves, or bending waves In U.S. Pat. No. 3,598,011 to Henkle, U.S. Pat. No. 3,884,109 to Johnson, U.S. Pat. No. 4,018,129 to Hollander, U.S. Pat. No. 4,334,455 to Beecher, U.S. Pat. No. 4,592,264 to Svobaba, U.S. Pat. No. 5,003,858 to Rowell, U.S. Pat. No. 5,889,222 to Burgess, U.S. Pat. No. 6,696,626 to Pagenkopf, U.S. Pat. No. 6,998,523 to Devuono, U.S. Pat. No. 7,342,160 to Alberti, U.S. Pat. No. 7,759,567, to Marvin, and U.S. Published Patent Applications 2003/0005808 to Mercer and 2005/0217455 to Zayia, various structural changes and additions to a stringed instrument body, tail pin and end pin are disclosed. None of these prior art references address the removal of interfering energy of the wolf note using a portable dissipating medium engaging the end pin of a cello's tail piece.

SUMMARY OF THE INVENTION

In view of the foregoing, it is a primary object of the subject invention to remove interfering vibrations or energy generated in and around a string of a violin family instrument using a portable dissipating medium. The dissipating medium can be any material with the correct shear wave velocity, such as a light weight, natural mineral tile or a similar man-made title. The dissipating material can have different geometric shapes for receipt on the surface of a floor with a top surface of the medium receiving an end pin of a cello's tail piece thereon.

Another key object of the invention is the removal of the wolf note, which is an unevenness, a beating sound or a physical stuttering of the bow across a pitch of the instrument. By removing the wolf note, there is an improved and faster response of the bow in playing selected notes, ease in ricochet of the bow, reduced drag on the bow and increased clarity of sound from the musical instrument.

Yet another object of the invention is through the use of the dissipating medium, the tuning of the tail piece and end pin become evident. Also, the medium, when properly tuned to different makes of cellos, provides a consistent response of the instrument regardless of different floor surfaces or ambient conditions in concert halls, music chambers, and indoor and outdoor theaters.

The subject invention includes a dissipating medium made of a tile with a specific shear wave velocity and size. The stone-like tile is preferably a tile made out of a natural mineral. In one preferred embodiment, the natural mineral is travertine. The tile can have an angular shape in a range of 10 to 12 inches square and a thickness in a range of ½ to ¾ inch. A top surface of the tile includes an annular depression centered thereon and adapted for receiving an end pin of a cello's tail piece. Also the dissipating medium can be constructed of two tiles, one on top of the other, with the upper tile 10 inches square and the lower tile 12 inches square. Obviously, the dissipating medium can have various angular and annular geometric shapes without departing from the spirit and scope of the invention. Also, the dissipating medium has a weight in a range of 6 to 12 pounds for ease in transporting when using it during the play of the cello.

These and other objects of the present invention will become apparent to those familiar with the construction and function of bowed string instruments when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the subject dissipating medium used with a stringed instrument, and in which:

FIG. 1 is a perspective view of a musician playing a cello. The cello having a tail piece with end pin received in a depression in a top surface of the subject portable dissipating medium. The medium is shown having first and second angular shaped tiles.

FIG. 2 is another perspective view of the musician and similar to FIG. 1. In this drawing, the end pin is received in a depression in a different geometric configuration of the dissipating medium. This medium is also shown having first and second angular shaped tiles.

FIG. 3 illustrates the dissipating medium as a single, angular shaped tile.

FIG. 4 shows the dissipating medium as a single annular shaped tile.

FIG. 5 illustrates the dissipating medium with first and second annular shaped tiles.

DETAILED DESCRIPTION OF THE PREFERRED EMBODIMENTS

Figure 6:
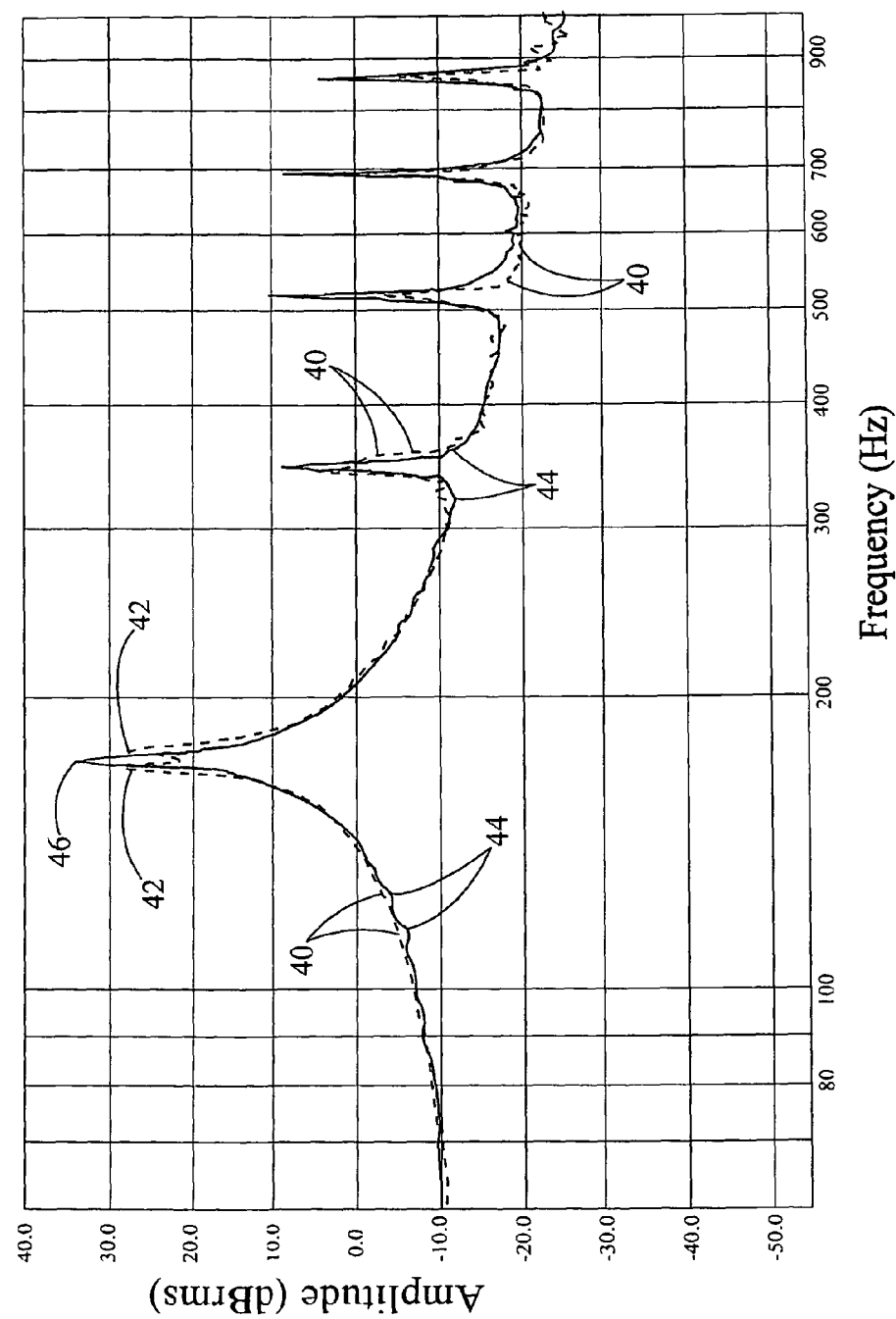
FIG. 6 is a Frequency and Amplitude spectrum graph illustrating the playing of the cello without the use of the dissipating medium and with the dissipating medium eliminating the wolf note in a range of 150 to 190 Hz and found between the notes E flat and F sharp.

In FIG. 1, a perspective view of a musician 10 is shown playing a cello 12, with sound waves 13 projecting outwardly from the cello. The cello 12 includes a tail piece 14 with end pin 16. Also, the cello 12 is shown with a cable 15 from the tail piece 14 to the end pin 16 to assist in the transfer of energy and vibrations from the cello strings to the end pin. The subject dissipating medium, having a general reference numeral 18, is shown in this example as a two-piece, natural mineral, square shaped, tile having a stone-like first tile 20 disposed on top of a stone-like second tile 22 and attached using an adhesive. A top surface 24 of the first tile 20 is shown having a depression 26 or hole centered thereon for receiving and holding the end pin 16 during the playing of the cello 12.

It has been found that "travertine" has proven to be an ideal natural mineral for the construction of the dissipating medium 18. Travertine can be cut easily, it is lightweight and it can be tuned, as a filter, with various makes of cellos to a proper shear wave velocity or Poisson's ratio of the mineral to eliminate the interfering energy of the wolf note. While travertine is mentioned, it should be keep in mind that other natural minerals and made-made materials, which may or may not be as effective or cost efficient, can be used in the construction of the dissipating medium 18. In this drawing, a shear wave 27 of the wolf note is shown dissipating outwardly from the sides of the dissipating medium 18.

In FIG. 1, the second tile 22 of the dissipating medium 18 is illustrated having a width "W" in a range of 11 to 12 inches, a length "L" in a range of 11 to 12 inches, and an overall thickness "T" of the two tiles of ½ to ¾ inches. These particular dimensions were calculated and then optimized by trial and error and proven to remove the interfering vibrations or "interfering energy" created during the playing of the wolf note by the cello 12. Also, the dissipating medium 18 prevents a reflection of the interfering energy back into the cello 12.

The weight of the two tiles is in a range of 6 to 12 pounds for ease in transporting the dissipating medium. This weight is kept as light as possible while still allowing for the dissipation of the interfering energy.

In FIG. 2, another perspective view of the musician 10 and cello 12 is shown and similar to FIG. 1. In this drawing, the end pin 14 is received in the depression 26 in the first tile 20 having an octagonal configuration. Obviously, the first and second tiles 20 and 22 can have different geometric configurations without departing from the spirit and scope of the invention. Also, variations in the depression 16 and material used to protect the dissipating medium 18 can vary without departing from the spirit and scope of the invention.

In FIG. 3, still another perspective view of the dissipating medium 18 is shown as an angular shaped, single piece tile 28. The single piece tile 28 has similar dimensions as the first and second tiles 20 and 22, shown in FIGS. 1 and 2.

In FIG. 4, yet another perspective view of the dissipating medium 18 is illustrated with an annular shaped, single piece tile 30 having a diameter "D" in a range of 11 to 12 inches and a thickness "T" in a range of ½ to ¾ inches.

In FIG. 5, the dissipating medium 18 is shown as an annular shaped, two piece tile 32. The two piece tile 32 includes a first tile 34 having a diameter "D1" in a range of 10 to 11 inches and a second tile 36 having the diameter "D" in the range of 11 to 12 inches. The overall thickness is also in a range of ½ to ¾ inches.

In FIG. 6, a Frequency and Amplitude spectrum graph is shown illustrating a frequency curve 40, in dashed lines, recorded when playing the cello 12 with the end pin 14 received on a carpet, a rug, a wood floor and like surface without the use of the dissipating medium 18. It is important to notice the wolf note appears as a double peak 42 in a narrow range of 170 to 180 Hz. Broadly, the double peak 42 of the wolf note appears in a range of 150 to 190 Hertz for different makes of cellos, when playing notes from E flat to F sharp.

Also illustrated in this drawings is another frequency curve 44, in solid lines, recorded when playing the cello 12 with the end pin 14 received in the depression 26 of the dissipating medium 18. But as discussed thoroughly above, by using the dissipating medium 18, the double peak 42, representing the unwanted wolf note, is eliminated and a sharp, single peak 46 appears on the solid line curve 44. Also, additionally partial frequencies of the wolf note now appear as a sharp, single peak in FIG. 6.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. A portable dissipating medium adapted for receiving an end pin of a cello's tail piece thereon and eliminating a wolf note played on a cello, the dissipating medium comprising:
a stone-like tile material having a horizontal top surface and a horizontal bottom surface, the bottom surface adapted for receipt on a floor, the top surface having a depression therein, the depression adapted for receiving the end pin therein, the stone-like material angular in shape and dimensioned in width, length and thickness or annular in shape and dimensioned in diameter and thickness, the stone-like material tuned to eliminate the wolf note and its related energy in a range of 150 to 190 Hz, E flat to F sharp, during the play of the cello.

2. The dissipating medium as described in claim 1 wherein the stone-like tile material is a natural occurring mineral.

3. The dissipating medium as described in claim 2 wherein the natural occurring mineral is travertine.

4. The dissipating medium as described in claim 1 wherein the stone-like tile material has a shear wave velocity between 300 and 400 m/sec.

5. The dissipating medium as described in claim 1 wherein the stone-like tile material has angular dimensions of a width in a range of 11 to 12 inches, a length in a range of 11 to 12 inches and a thickness in a range of ½ to ¾ inches.

6. The dissipating medium as described in claim 1 wherein the stone-like material has a diameter in a range of 11 to 12 inches and a thickness in a range of ½ to ¾ inches.

7. A portable dissipating medium adapted for receiving an end pin of a cello's tail piece thereon and eliminating a wolf note played on a cello, the dissipating medium comprising:
a stone-like, natural occurring mineral, tile material having a horizontal top surface and a horizontal bottom surface, the bottom surface adapted for receipt on a floor, the top surface having a depression therein, the depression adapted for receiving the end pin therein, the stone-like material angular in shape and dimensioned in width, length and thickness or annular in shape and dimensioned in diameter and thickness, the stone-like material tuned to eliminate the wolf note and its related energy in a range of 150 to 190 Hz, E flat to F sharp, during the play of the cello.

8. The dissipating medium as described in claim 7 wherein the stone-like material has a shear wave velocity between 300 and 400 m/sec.

9. The dissipating medium as described in claim 7 wherein the stone-like material has angular dimensions of a width in a range of 11 to 12 inches, a length in a range of 11 to 12 inches and a thickness in a range of ½ to ¾ inches.

10. The dissipating medium as described in claim 7 wherein the stone-like material has a diameter in a range of 11 to 12 inches and a thickness in a range of ½ to ¾ inches.

11. A portable dissipating medium adapted for receiving an end pin of a cello's tail piece thereon and eliminating a wolf note and its related energy played on a cello, the dissipating medium comprising:
a stone-like first tile disposed on top of a stone-like second tile and attached thereto, a top surface of the first tile having a depression centered thereon and adapted for receiving and holding the end pin during the playing of the cello, the first and second stone-like tiles are angular in shape and dimensioned in width, length and thickness or annular in shape and dimensioned in a diameter and thickness, the stone-like tiles tuned to remove a wolf note in a range of 150 to 190 Hz, E flat to F sharp, during the play of the cello.

12. The dissipating medium as described in claim 11 wherein the first and second stone-like tiles are made of a natural occurring mineral.

13. The dissipating medium as described in claim 12 wherein the natural occurring mineral is travertine.

14. The dissipating medium as described in claim 11 wherein the first stone-like tile has angular dimensions of a width in a range of 10 to 11 inches and a length in a range of 10 to 11 and the second stone-like tile has angular dimensions of a width in a range of 11 to 12 inches and a length in a range of 11 to 12 inches, the first and second stone-like tiles having an overall thickness in a range of ½ to ¾ inches.

15. The dissipating medium as described in claim 11 wherein the first stone-like tile has a diameter in a range of 10 to 11 inches and the second stone-like tile has a diameter in a range of 11 to 12 inches, the first and second stone-like tiles having an overall thickness in a range of ½ to ¾ inches.

* * * * *